United States Patent
Dawoodjee et al.

(10) Patent No.: US 12,274,852 B1
(45) Date of Patent: Apr. 15, 2025

(54) HERMETIC SEAL TESTER FOR MEDICAL DEVICES AND PROCESS FOR TESTING MEDICAL DEVICE INTEGRITY WITH A HERMETIC SEAL TESTER

(71) Applicants: John Dawoodjee, Canoga Park, CA (US); William Shane Manor, Canoga Park, CA (US)

(72) Inventors: John Dawoodjee, Canoga Park, CA (US); William Shane Manor, Canoga Park, CA (US)

( * ) Notice: Subject to any disclaimer, the term of this patent is extended or adjusted under 35 U.S.C. 154(b) by 811 days.

(21) Appl. No.: 17/373,405

(22) Filed: Jul. 12, 2021

Related U.S. Application Data

(60) Provisional application No. 63/057,740, filed on Jul. 28, 2020.

(51) Int. Cl.
| | |
|---|---|
| *A61M 39/00* | (2006.01) |
| *A61M 39/10* | (2006.01) |
| *A61M 39/16* | (2006.01) |
| *A61M 39/24* | (2006.01) |
| *A61M 39/26* | (2006.01) |
| *A61B 17/16* | (2006.01) |

(52) U.S. Cl.
CPC ........ *A61M 39/1011* (2013.01); *A61M 39/16* (2013.01); *A61M 39/24* (2013.01); *A61M 39/26* (2013.01); *A61B 17/16* (2013.01); *A61M 2039/1005* (2013.01); *A61M 2205/15* (2013.01); *A61M 2205/3331* (2013.01)

(58) Field of Classification Search
CPC ....... A61M 39/1011; H01L 21/28; A61N 1/04
See application file for complete search history.

(56) References Cited

U.S. PATENT DOCUMENTS

| | | | | |
|---|---|---|---|---|
| 6,491,625 | B1* | 12/2002 | Newton | A61B 1/00057 |
| | | | | 73/45.5 |
| 2001/0032494 | A1* | 10/2001 | Greszler | A61B 1/125 |
| | | | | 73/40 |
| 2002/0001537 | A1* | 1/2002 | Hlebovy | A61B 1/123 |
| | | | | 422/28 |
| 2005/0189027 | A1* | 9/2005 | Markham | F16L 55/124 |
| | | | | 138/93 |

FOREIGN PATENT DOCUMENTS

| | | | |
|---|---|---|---|
| CN | 203337338 U | * | 12/2013 |
| CN | 205333251 U | * | 6/2016 |
| CN | 214149722 U | * | 9/2021 |
| CN | 216078702 U | * | 3/2022 |
| JP | H0657307 U | * | 8/1994 |
| WO | WO-2021258710 A1 | * | 12/2021 ......... G01M 13/005 |

* cited by examiner

Primary Examiner — John R Downey
Assistant Examiner — Anant A Gupta
(74) Attorney, Agent, or Firm — Plager Schack LLP; Mark H. Plager, Esq.; Stephen Hallberg, Esq.

(57) ABSTRACT

A hermetic seal tester for medical devices and a process for testing medical device integrity with a hermetic seal tester are disclosed. The hermetic seal tester for medical devices detects internal seal leaks, if any, by performing the process for testing medical device integrity with a hermetic seal tester prior to every use of a medical device, instrument or medical power tool. A leak can cause medical device or power tool failure during surgery. Leaks within the fluid pathway also compromise the ability to clean and sterilize the medical device or power tool, resulting in the potential for cross-contamination. Preventive maintenance is far superior to waiting until the medical device or power tool fails.

14 Claims, 9 Drawing Sheets

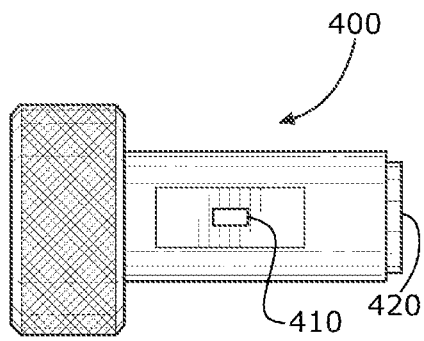 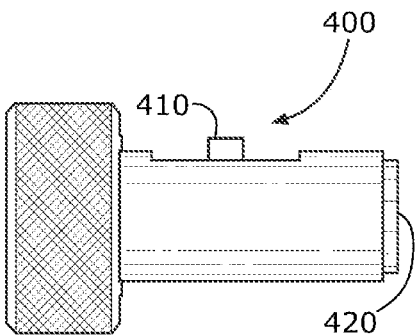 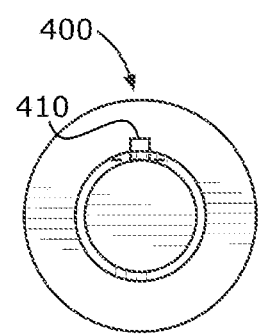
FIG. 4A　　　　FIG. 4B　　　　FIG. 4C
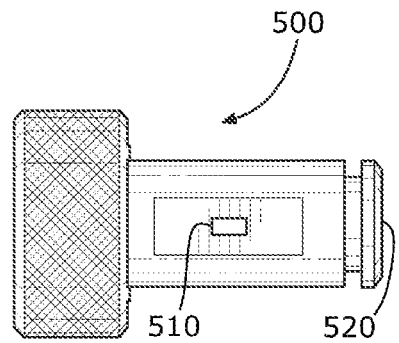 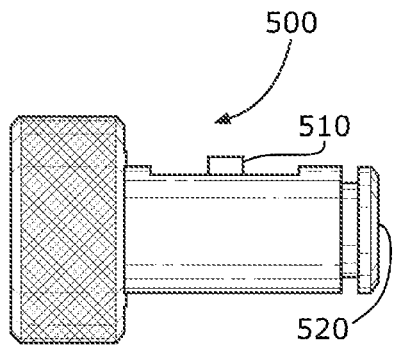 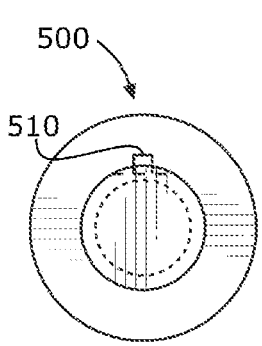
FIG. 5A　　　　FIG. 5B　　　　FIG. 5C
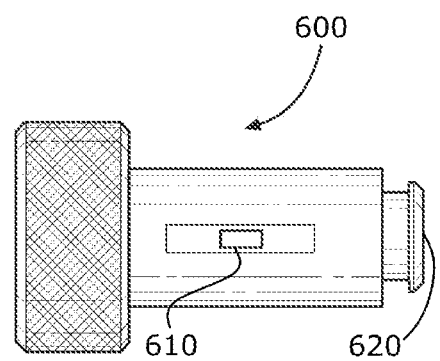 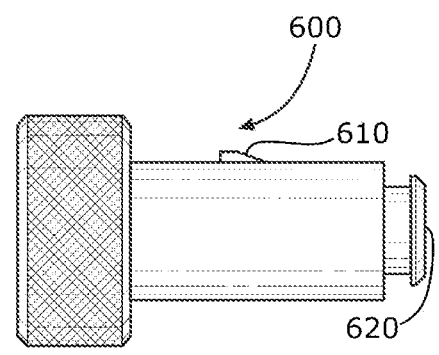 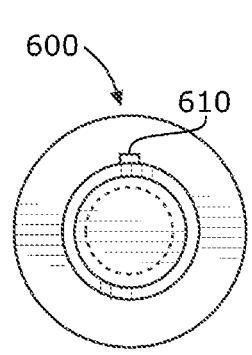
FIG. 6A　　　　FIG. 6B　　　　FIG. 6C

HERMETIC SEAL TESTER FOR MEDICAL DEVICES AND PROCESS FOR TESTING MEDICAL DEVICE INTEGRITY WITH A HERMETIC SEAL TESTER

CLAIM OF BENEFIT TO PRIOR APPLICATION

This application claims benefit to U.S. Provisional Patent Application 63/057,740, entitled "HERMETIC SEAL TESTER FOR MEDICAL POWER TOOLS," filed Jul. 28, 2020. The U.S. Provisional Patent Application 63/057,740 is incorporated herein by reference.

BACKGROUND

Embodiments of the invention described in this specification relate generally to devices to test for leaks and defective seals, and more particularly, to a hermetic seal tester for medical devices and a process for testing medical device integrity with a hermetic seal tester.

During the course of a medical procedure, interior seals on medical power tools, medical instruments, or any other medical devices (hereinafter referred to collectively and individually as "medical device" in the singular sense and "medical devices" in the plural sense) may fail thus allowing fluid leakage into the power tool housing and motor or other operational components of the medical device. The leaked fluid can cause the power tool or other medical device to become inoperable during surgery. Leaks within the fluid pathway also compromise the ability to clean and sterilize the medical device, resulting in the potential for cross-contamination.

As such, preventive maintenance is far superior to waiting until the medical device fails and allows for repair rather than equipment replacement. However, human detection is not possible until the device fails.

Therefore, what is needed is a way to detect internal seal leaks, if any, prior to every use of a medical device, instrument, or medical power tool.

BRIEF DESCRIPTION

A novel hermetic seal tester for medical devices and a novel process for testing medical device integrity with a hermetic seal tester are disclosed. In some embodiments, the hermetic seal tester for medical devices and the process for testing medical device integrity with a hermetic seal tester detect defective seals or leaks, if any, prior to every use. By this manner of preventive maintenance, the hermetic seal tester for medical devices and the process for testing medical device integrity with a hermetic seal tester help to avoid failure during surgery and allow for repair rather than equipment replacement.

In some embodiments, the hermetic seal tester comprises (i) a plug, (ii) a pump, (iii) a gauge, and (iv) tubing. In some embodiments, the pump is activated to monitor pressure within the medical device as displayed on the gauge. In some embodiments, the medical device being tested is a medical power tool. In some embodiments, the medical device being tested is a bone shaver medical device.

In some embodiments, the hermetic seal tester comprises (i) a nylon plug/stop coupled to a distal tip of a channel port of a medical device being tested for leaks, (ii) a hand pressure pump operably connected to a proximal end of the medical device, (iii) a pressure gauge operably connected to the pump, and (iv) silicon tubing. In some embodiments, the hermetic seal tester further comprises silicone O-rings.

In some embodiments, several different types of nylon plugs are supported for use with the hermetic seal tester, each with different diameters, lengths, shapes, or configurations. In some embodiments, the nylon plug of the hermetic seal tester attaches to the distal tip of the channel port of the medical device being tested to form an air tight seal. In some embodiments, the hand pressure pump with the gauge attaches to the proximal end of the channel with the silicon tubing. The pressure applied through the channel measures the integrity of the internal seals of the medical device prior to use.

In some other embodiments, the nylon plug fits on the distal tip of the channel port of the medical device and is snapped into place to create an air tight seal with the silicon O-rings. In these embodiments, the pressure pump with pressure gauge is connected to the proximal end of the medical device with the silicon tubing. The pressure gauge is configured to detect any leakage in the internal channel when pressure is applied using the hand pressure pump.

In some embodiments, the process for testing medical device integrity with a hermetic seal tester comprises inserting a hermetic seal testing stop into a distal end of a medical device being tested for leaks by a user with a hermetic seal tester, connecting an open end of tubing of the hermetic seal tester to a discharge port at a proximal end of the medical device, ensuring that a relief valve of a pump of the hermetic seal tester is in a closed position, applying force to squeeze the pump to increase pressure within an interior channel of the medical device, observing a pressure reading of a pressure gauge of the hermetic seal tester, determining whether the pressure gauge holds the pressure reading, and confirming one of (i) affirmative integrity of the medical device when the pressure gauge holds the pressure reading and (ii) no integrity of the medical device when the pressure gauge does not hold the pressure reading.

The preceding Summary is intended to serve as a brief introduction to some embodiments of the invention. It is not meant to be an introduction or overview of all inventive subject matter disclosed in this specification. The Detailed Description that follows and the Drawings that are referred to in the Detailed Description will further describe the embodiments described in the Summary as well as other embodiments. Accordingly, to understand all the embodiments described by this document, a full review of the Summary, Detailed Description, and Drawings is needed. Moreover, the claimed subject matters are not to be limited by the illustrative details in the Summary, Detailed Description, and Drawings, but rather are to be defined by the appended claims, because the claimed subject matter can be embodied in other specific forms without departing from the spirit of the subject matter.

BRIEF DESCRIPTION OF THE DRAWINGS

Having described the invention in general terms, reference is now made to the accompanying drawings, which are not necessarily drawn to scale, and wherein:

FIG. 4A conceptually illustrates a top view of a first type of nylon plug of a hermetic seal tester in some embodiments.

FIG. 4B conceptually illustrates a side view of the first type of nylon plug of the hermetic seal tester in some embodiments.

FIG. 4C conceptually illustrates a front view of the first type of nylon plug of the hermetic seal tester in some embodiments.

FIG. 5A conceptually illustrates a top view of a second type of nylon plug of a hermetic seal tester in some embodiments.

FIG. 5B conceptually illustrates a side view of the second type of nylon plug of the hermetic seal tester in some embodiments.

FIG. 5C conceptually illustrates a front view of the second type of nylon plug of the hermetic seal tester in some embodiments.

FIG. 6A conceptually illustrates a top view of a third type of nylon plug of a hermetic seal tester in some embodiments.

FIG. 6B conceptually illustrates a side view of the third type of nylon plug of the hermetic seal tester in some embodiments.

FIG. 6C conceptually illustrates a front view of the third type of nylon plug of the hermetic seal tester in some embodiments.

DETAILED DESCRIPTION

In the following detailed description of the invention, numerous details, examples, and embodiments of the invention are described. However, it will be clear and apparent to one skilled in the art that the invention is not limited to the embodiments set forth and that the invention can be adapted in several manners. In particular, it shall be appreciated that the components of the hermetic seal tester described in several embodiments herein may comprise any alternative known materials in the field and be of any color, configuration, size, and/or dimensions. It shall also be appreciated that the components of the hermetic seal tester described herein may be manufactured and assembled using any known techniques in the field.

Some embodiments of the invention provide a novel hermetic seal tester for medical devices and a process for testing medical device integrity with a hermetic seal tester. In some embodiments, the hermetic seal tester for medical devices and the process for testing medical device integrity with a hermetic seal tester detect defective seals or leaks, if any, prior to every use. Leaks within the fluid pathway also compromise the ability to clean and sterilize the medical device, resulting in the potential for cross-contamination. By this manner of preventive maintenance, the hermetic seal tester for medical devices and the process for testing medical device integrity with a hermetic seal tester help to avoid failure during surgery, allow for repair rather than equipment replacement, and reduce the potential for cross-contamination.

In some embodiments, the hermetic seal tester comprises (i) a plug, (ii) a pump, (iii) a gauge, and (iv) tubing. In some embodiments, the pump is activated to monitor pressure within the medical device as displayed on the gauge. In some embodiments, the medical device being tested is a medical power tool. In some embodiments, the medical device being tested is a bone shaver medical device.

In some embodiments, the hermetic seal tester comprises (i) a nylon plug/stop coupled to a distal tip of a channel port of a medical device being tested for leaks, (ii) a hand pressure pump operably connected to a proximal end of the medical device, (iii) a pressure gauge operably connected to the pump, and (iv) silicon tubing. In some embodiments, the hermetic seal tester further comprises silicone O-rings.

Figure 1:
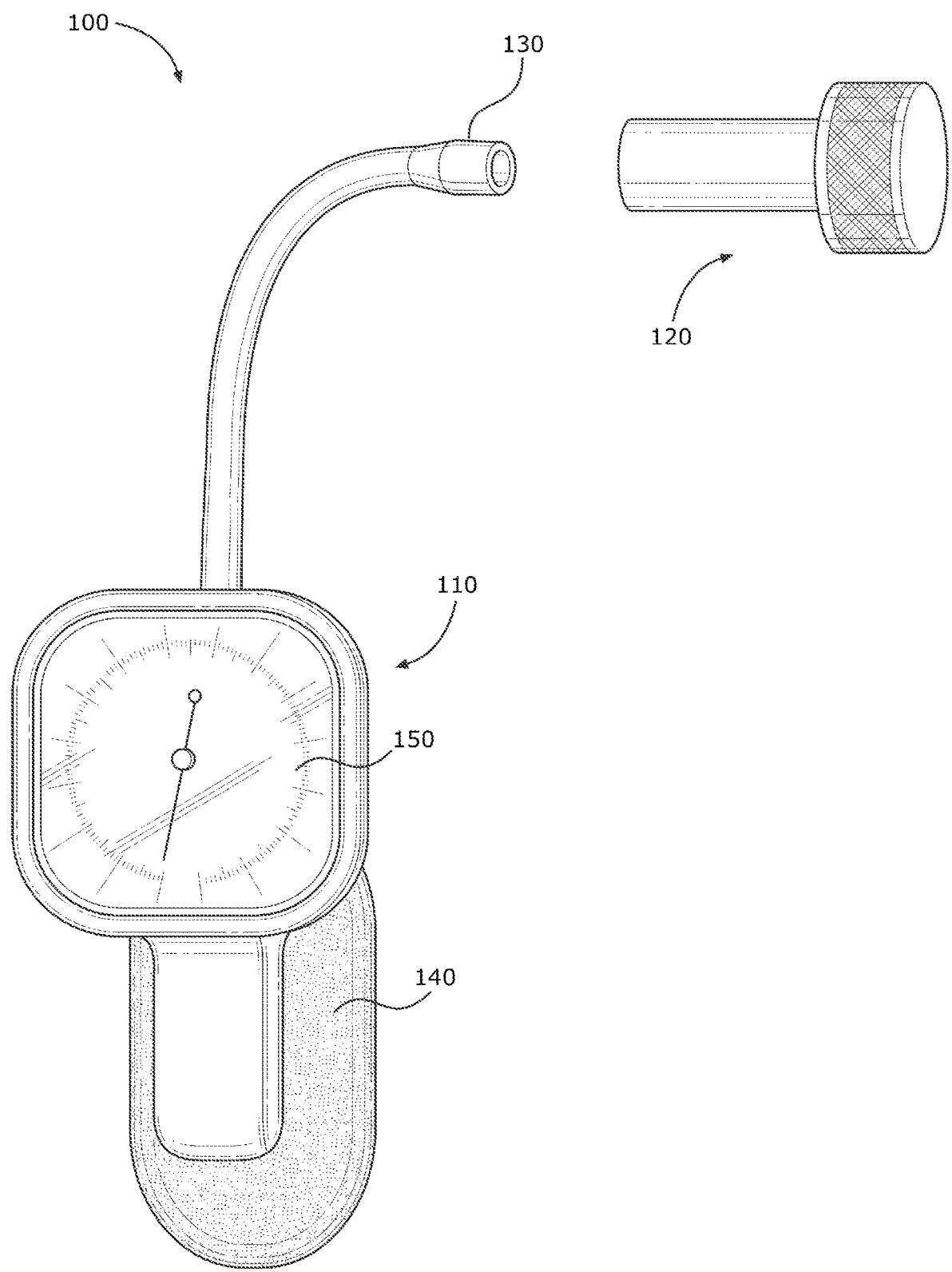
FIG. 1 conceptually illustrates a hermetic seal tester in some embodiments.

By way of example, FIG. 1 conceptually illustrates a hermetic seal tester 100 in some embodiments. As shown in this figure, the hermetic seal tester 100 comprises a hand pressure pump with gauge 110, a nylon plug 120, tubing 130, a hand pressure pump 140, and a gauge 150. To operate the hermetic seal tester 100, a medical device, such as a medical power tower (e.g., an arthroscopic shaver or other medical power or pneumatic tool used in the field), is attached between the tubing 130 and the nylon plug 120. This is further described below, by reference to FIGS. 2-3 and 12-14.

As stated above, during the course of a medical procedure, interior seals on medical power tools, medical instruments, or any other medical devices (hereinafter referred to collectively and individually as "medical device" in the singular sense and "medical devices" in the plural sense) may fail thus allowing fluid leakage into the power tool housing and motor or other operational components of the medical device. The leaked fluid can cause the power tool or other medical device to become inoperable during surgery. Leaks within the fluid pathway also compromise the ability to clean and sterilize the medical device, resulting in the potential for cross-contamination. As such, preventive maintenance is far superior to waiting until the medical device fails and allows for repair rather than equipment replacement. However, human detection is not possible until the device fails. Embodiments of the invention described in this specification solve such problems by attaching the nylon plug of the hermetic seal tester to the distal tip of the channel port of a medical device to form an air tight seal. A hand pressure pump with a gauge attaches to the proximal end of the channel with a silicon tube. The pressure applied through the channel measures the integrity of the internal seals prior to use.

Figure 2:
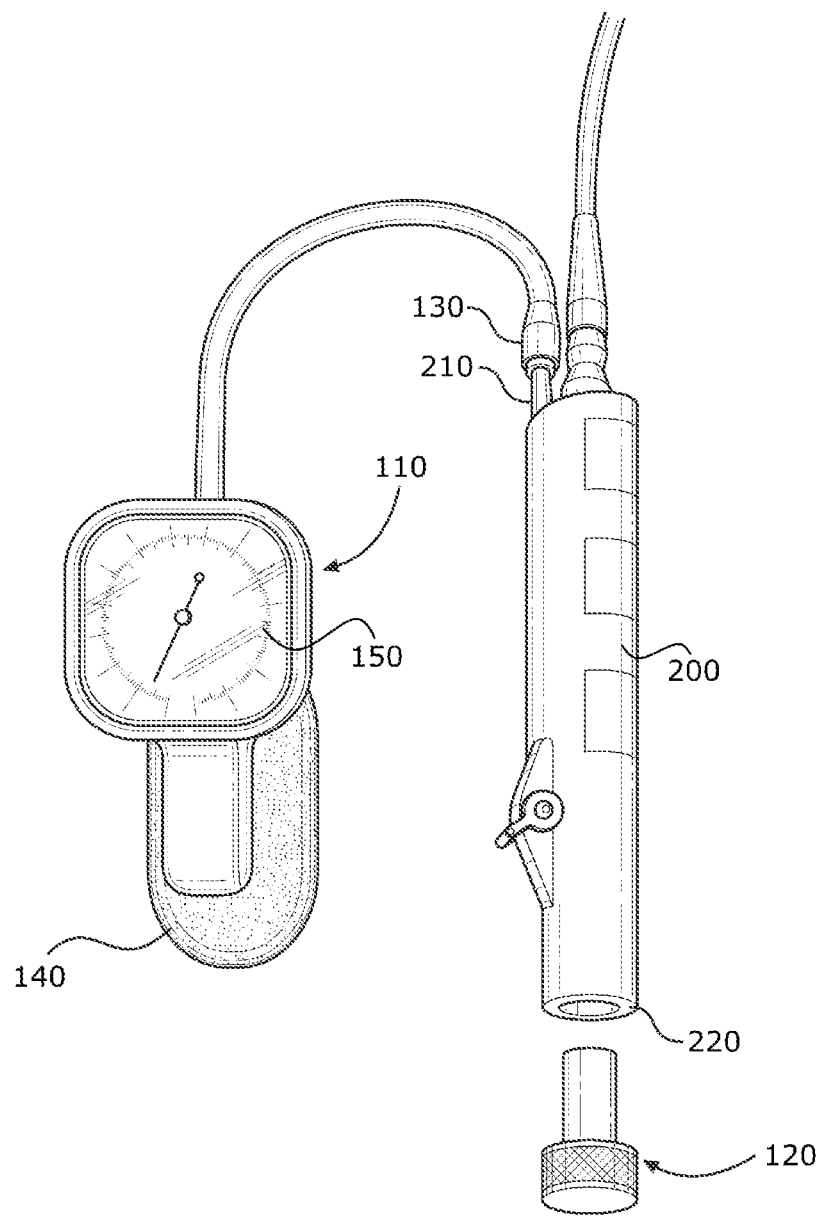
FIG. 2 conceptually illustrates the hermetic seal tester and a medical device to be tested by the hermetic seal tester in some embodiments.

By way of example, FIG. 2 conceptually illustrates the hermetic seal tester 100 and a medical device 200 to be tested by the hermetic seal tester in some embodiments. As shown in this figure, the medical device 200 is connected to the tubing 130 at the proximal end 210 of the medical device 200. However, in this figure, the nylon plug 120 is not attached and the distal end 220 of the fluid channel of the medical device 200 remains open. The hermetic seal tester 100 is operational only after the nylon plug 120 is connected to and seals off the distal end 220 of the medical device 200. This is demonstrated next, in FIG. 3.

Figure 3:
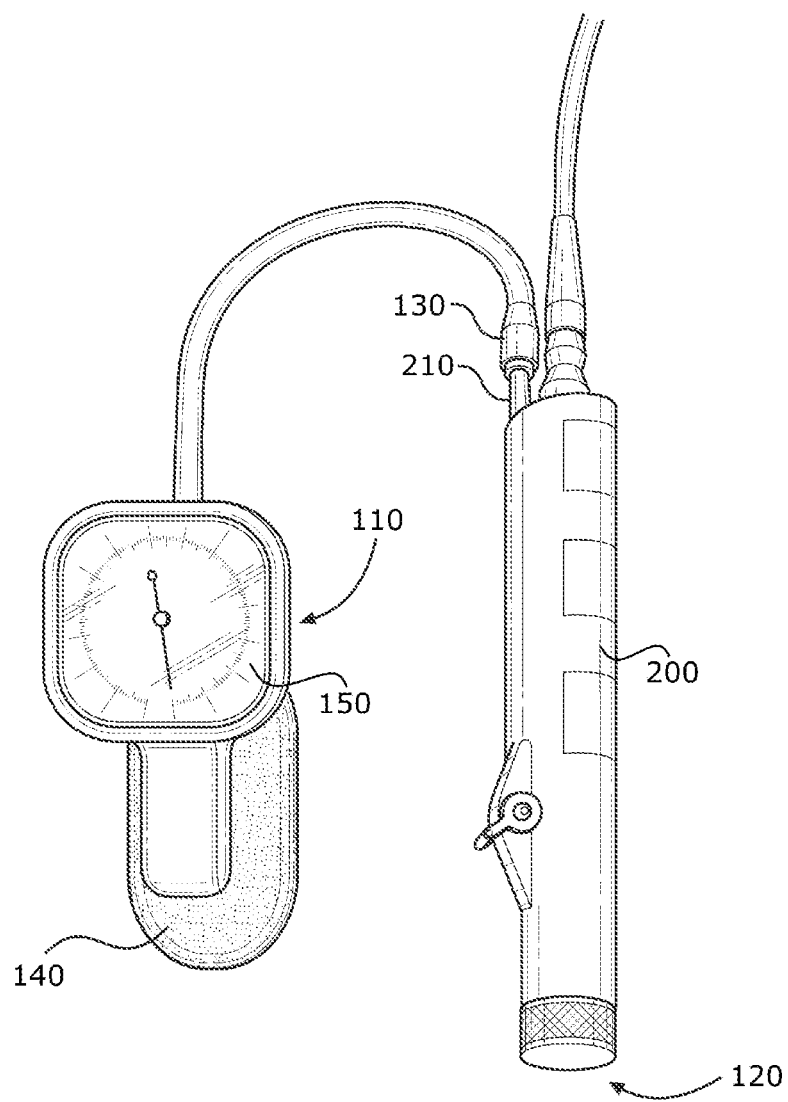
FIG. 3 conceptually illustrates the hermetic seal tester in use for testing the medical device in some embodiments.

Specifically, FIG. 3 conceptually illustrates the hermetic seal tester 100 in use for testing the medical device 200 in some embodiments. As shown in this figure, the medical device 200 is connected to the tubing 130 at the proximal end 210 of the medical device 200 and now the nylon plug 120 is connected to the distal end 220 of the medical device 200. The distal end 220 of a medical power tool, for example, may be a distal tip of a channel port at the end of a fluid channel of the medical power tool. Connecting the nylon plug 120 to the distal end 220 of the medical device 200 has the effect of sealing off the fluid channel within the medical device 200. In this configuration, a user can operate the hand pressure pump 140 to test the medical device 200 for leaks, as displayed on the gauge 150.

Embodiments of the hermetic seal tester for medical devices and the process for testing medical device integrity with a hermetic seal tester described in this specification differ from and improve upon currently existing options. In particular, there are no similar devices, apparatuses, or methods similar to the hermetic seal tester for medical devices or the process for testing medical device integrity with a hermetic seal tester to date. Previous means of detecting seal leaks was when the medical power tool would no longer operate. The medical power tool or medical device would need to be replaced or rebuilt. By contrast, the hermetic seal tester for medical devices detects compromised seals, if any, prior to every use by way of the process for testing medical device integrity with a hermetic seal tester.

The hermetic seal tester for medical devices and the process for testing medical device integrity with a hermetic seal tester of the present disclosure may be comprised of the following elements. This list of possible constituent elements is intended to be exemplary only and it is not intended that this list be used to limit the hermetic seal tester for medical devices and the process for testing medical device integrity with a hermetic seal tester of the present application to just these elements. Persons having ordinary skill in the art relevant to the present disclosure may understand there to be equivalent elements that may be substituted within the present disclosure without changing the essential function or operation of the hermetic seal tester for medical devices and the process for testing medical device integrity with a hermetic seal tester.
 1. Nylon plugs with different diameters, lengths, shapes, or configurations (examples of several different types of nylon plugs are described below)
 2. Silicon O-rings in some embodiments of the hermetic seal tester
 3. Hand Pressure Pump with Gauge
 4. Silicon Tubing (or other tubing suitable for the medical device application)

The various elements of the hermetic seal tester for medical devices and the process for testing medical device integrity with a hermetic seal tester of the present disclosure may be related in the following exemplary fashion. It is not intended to limit the scope or nature of the relationships between the various elements and the following examples are presented as illustrative examples only. The nylon plug (1) fits on the distal tip of the channel port of a medical power tool (or other medical device) and is snapped into place to create an air tight seal. In some embodiments, silicon O-rings (2) ensure the seal is air tight. A pressure pump with gauge (3) is connected to the proximal end of the medical power tool with silicon tubing (4). The pressure relief valve is closed. Pressure is applied using the hand pressure pump and the gauge detects any leakage in the internal channel.

In some embodiments, several different types of nylon plugs are supported for use with the hermetic seal tester, each with different diameters, lengths, shapes, or configurations. In some embodiments, the nylon plug of the hermetic seal tester attaches to the distal tip of the channel port of the medical device being tested to form an air tight seal. In some embodiments, the hand pressure pump with the gauge attaches to the proximal end of the channel with the silicon tubing. The pressure applied through the channel measures the integrity of the internal seals of the medical device prior to use.

In some other embodiments, the nylon plug fits on the distal tip of the channel port of the medical device and is snapped into place to create an air tight seal with the silicon O-rings. In these embodiments, the pressure pump with pressure gauge is connected to the proximal end of the medical device with the silicon tubing. The pressure gauge is configured to detect any leakage in the internal channel when pressure is applied using the hand pressure pump.

As noted above, several different types of nylon plugs are supported for use with the hermetic seal tester. The different type of nylon plugs differ by diameter, length, shape, or configuration. Several different types of nylon plugs are described next by reference to FIGS. 4A-C, 5A-C, 6A-C, 7A-C, and 8A-B.

By way of a first exemplary type of nylon plug, FIG. 4A conceptually illustrates a top view of a first type of nylon plug 400 of a hermetic seal tester in some embodiments. The first type of nylon plug 400 may be suitable for sealing off the distal end of a particular medical device or medical power tool, but may be unsuitable for sealing off the distal end of other medical devices or medical power tools. As shown in this figure, the first type of nylon plug 400 comprises a guide tab 410 and a plug end 420 with a first particular shape for sealing the distal tip of the channel port of the medical device to be tested by the hermetic seal tester. Turning to FIG. 4B, a side view of the first type of nylon plug 400 of the hermetic seal tester is conceptually illustrated. From this side view, the guide tab 410 is shown within a slight cut-out area along the length of the first type of nylon plug 400 and the plug end 420 having a slightly smaller diameter than the diameter along most of the length of the first type of nylon plug 400. This is reinforced in another view, shown in FIG. 4C, which conceptually illustrates a front view of the first type of nylon plug 400 of the hermetic seal tester with the guide tab 410 shown.

Now turning to a second exemplary type of nylon plug, FIG. 5A conceptually illustrates a top view of a second type of nylon plug 500 of a hermetic seal tester in some embodiments. Along with this top view, FIG. 5B conceptually illustrates a side view of the second type of nylon plug 500 and FIG. 5C conceptually illustrates a front view of the second type of nylon plug 500. The second type of nylon plug 500 has some similarities to and differences from the first type of nylon plug 400. For instance, like the guide tab 410 for the first type of nylon plug 400, the second type of nylon plug 500 has a guide tab 510 that is shown within a slight cut-out area along its length. However, the plug end 420 of the first type of nylon plug 400 is different from a plug end 520 of the second type of nylon plug 500. Therefore, the second type of nylon plug 500 may not be suitable for sealing off the distal end of those medical devices or medical power tools sealed off by the first type of nylon plug 400. Nevertheless, by providing another fitting length, diameter, shape, or configuration, the second type of nylon plug 500 ensures that the hermetic seal tester can effectively test a wider array of medical devices or medical power tools for leaks.

In another example, FIG. 6A conceptually illustrates a top view of a third type of nylon plug 600 of a hermetic seal tester in some embodiments. As shown in this figure, the third type of nylon plug 600 comprises a guide tab 610 and a plug end 620. Both the guide tab 610 and the plug end 620 differ from the guide tabs 410 and 510 and the plug ends 420 and 520 of the first and second types of nylon plugs 400 and 500. The third type of nylon plug 600 is further demonstrated in a side view conceptually illustrated in FIG. 6B and in a front view conceptually illustrated in FIG. 6C. Of particular note, the side view shown in FIG. 6B shows that there is not slight cut-out area along its length, unlike the first and second types of nylon plugs 400 and 500. Accordingly, the third type of nylon plug 600 may be suitable for sealing off the distal end of yet other medical devices or medical power tools that would not be effectively sealed off by either the first type of nylon plug 400 or the second type of nylon plug 500.

Figure 7A:
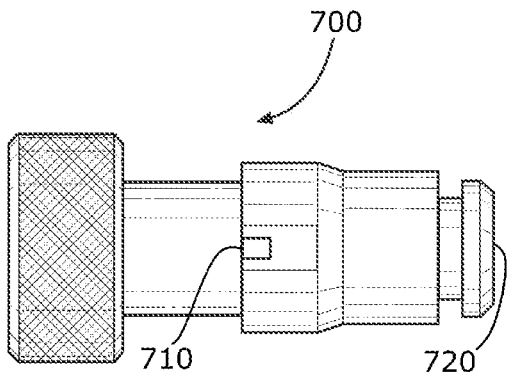
FIG. 7A conceptually illustrates a top view of a fourth type of nylon plug of a hermetic seal tester in some embodiments.
Figure 7B:
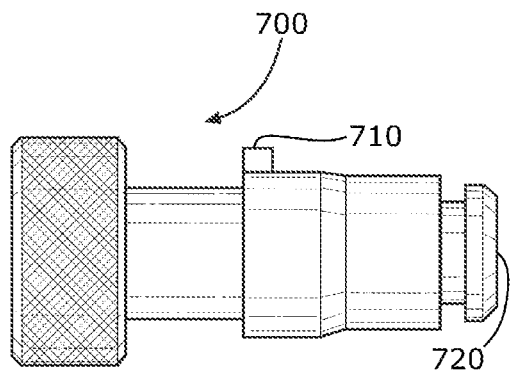
FIG. 7B conceptually illustrates a side view of the fourth type of nylon plug of the hermetic seal tester in some embodiments.
Figure 7C:
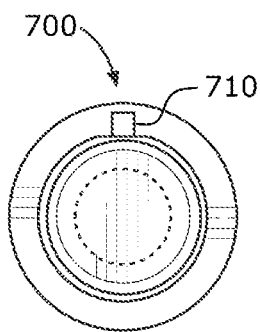
FIG. 7C conceptually illustrates a front view of the fourth type of nylon plug of the hermetic seal tester in some embodiments.
Figure 8A:
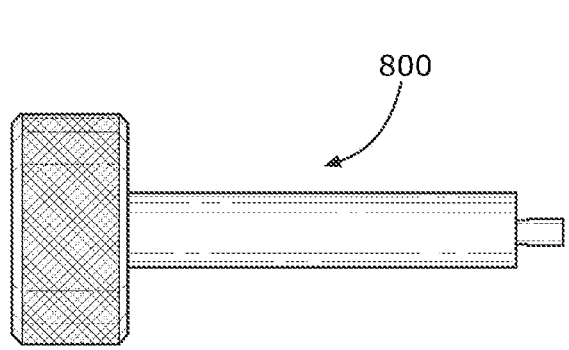
FIG. 8A conceptually illustrates a top view of a fifth type of nylon plug of a hermetic seal tester in some embodiments.
Figure 8B:
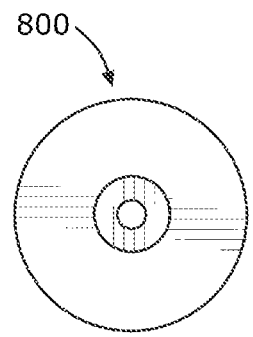
FIG. 8B conceptually illustrates a front view of the fifth type of nylon plug of the hermetic seal tester in some embodiments.

A fourth exemplary type of nylon plug is described by reference to FIGS. 7A-C. Specifically, FIG. 7A conceptually illustrates a top view of a fourth type of nylon plug 700 of a hermetic seal tester in some embodiments. Other views of the fourth type of nylon plug 700 are shown in FIG. 7B, which conceptually illustrates a side view of the fourth type of nylon plug 700, and in FIG. 7C, which conceptually illustrates a front view of the fourth type of nylon plug 700. As with the first, second, and third types of nylon plugs, the fourth type of nylon plug 700 comprises a guide tab 710 and a plug end 720, each of which vary in one way or another from the guide tabs and plug ends of the first, second, and third types of nylon plugs. Furthermore, different diameters along the length of the fourth type of nylon plug 700 are demonstrated, with the guide tab 710 positioned atop a section with a bigger diameter.

While the first, second, third, and fourth types of nylon plugs 400, 500, 600, and 700, described above by reference to FIGS. 4A-C, FIGS. 5A-C, FIGS. 6A-C, and FIGS. 7A-C, respectively, differ in some manner, such as diameter, length, shape of plug end, or configuration of guide tab, yet another type of nylon plug differs by diameter, length, shape, inclusion of components. Specifically, FIG. 8A conceptually illustrates a top view of a fifth type of nylon plug 800 of a hermetic seal tester in some embodiments. In another view, FIG. 8B conceptually illustrates a front view of the fifth type of nylon plug 800. As shown in these figures, the fifth type of nylon plug 800 does not have a guide tab and the diameter of the shaft that fits into the fluid channel of the medical device or medical power tool is considerably smaller than the diameters of the other exemplary nylon plugs described above. Furthermore, the plug end of the fifth type of nylon plug 800 has an even smaller diameter. With this configuration, the fifth type of nylon plug 800 would not be suitable to seal off the distal ends of the medical devices/medical power tools that could be effectively sealed by any of the first, second, third, and fourth types of nylon plugs 400, 500, 600, and 700. However, the fifth type of nylon plug 800 could be effectively snapped into place for other medical devices or medical power tools that have narrower channel ports, and therefore, smaller distal tips, and thereby create an air tight seal to allow the hermetic seal tester to effectively and accurately test the medical device for leaks or cracks.

In some embodiments, the process for testing medical device integrity with a hermetic seal tester comprises inserting a hermetic seal testing stop into a distal end of a medical device being tested for leaks by a user with a hermetic seal tester, connecting an open end of tubing of the hermetic seal tester to a discharge port at a proximal end of the medical device, ensuring that a relief valve of a pump of the hermetic seal tester is in a closed position, applying force to squeeze the pump to increase pressure within an interior channel of the medical device, observing a pressure reading of a pressure gauge of the hermetic seal tester, determining whether the pressure gauge holds the pressure reading, and confirming one of (i) affirmative integrity of the medical device when the pressure gauge holds the pressure reading and (ii) no integrity of the medical device when the pressure gauge does not hold the pressure reading.

The hermetic seal tester for medical devices and the process for testing medical device integrity with a hermetic seal tester of the present disclosure generally works by attaching or fitting the nylon plug on or to the distal tip of the channel port of a medical power tool, thereby creating an air tight seal on the distal end of the medical power tool. Connecting the hand pressure pump with the gauge to the proximal of the medical power tool with the silicon tubing allows for air pressure to be pumped into the interior channel of the device. If there are any defective seals or leaks the hand pump pressure gauge needle will show decreased pressure. For example, pressure may increase as a user squeezes the hand pump and the gauge may reflect the increased pressure in its dial reading, but if pressure quickly or even slowly dissipates, then there is a leak detected.

Figure 9:
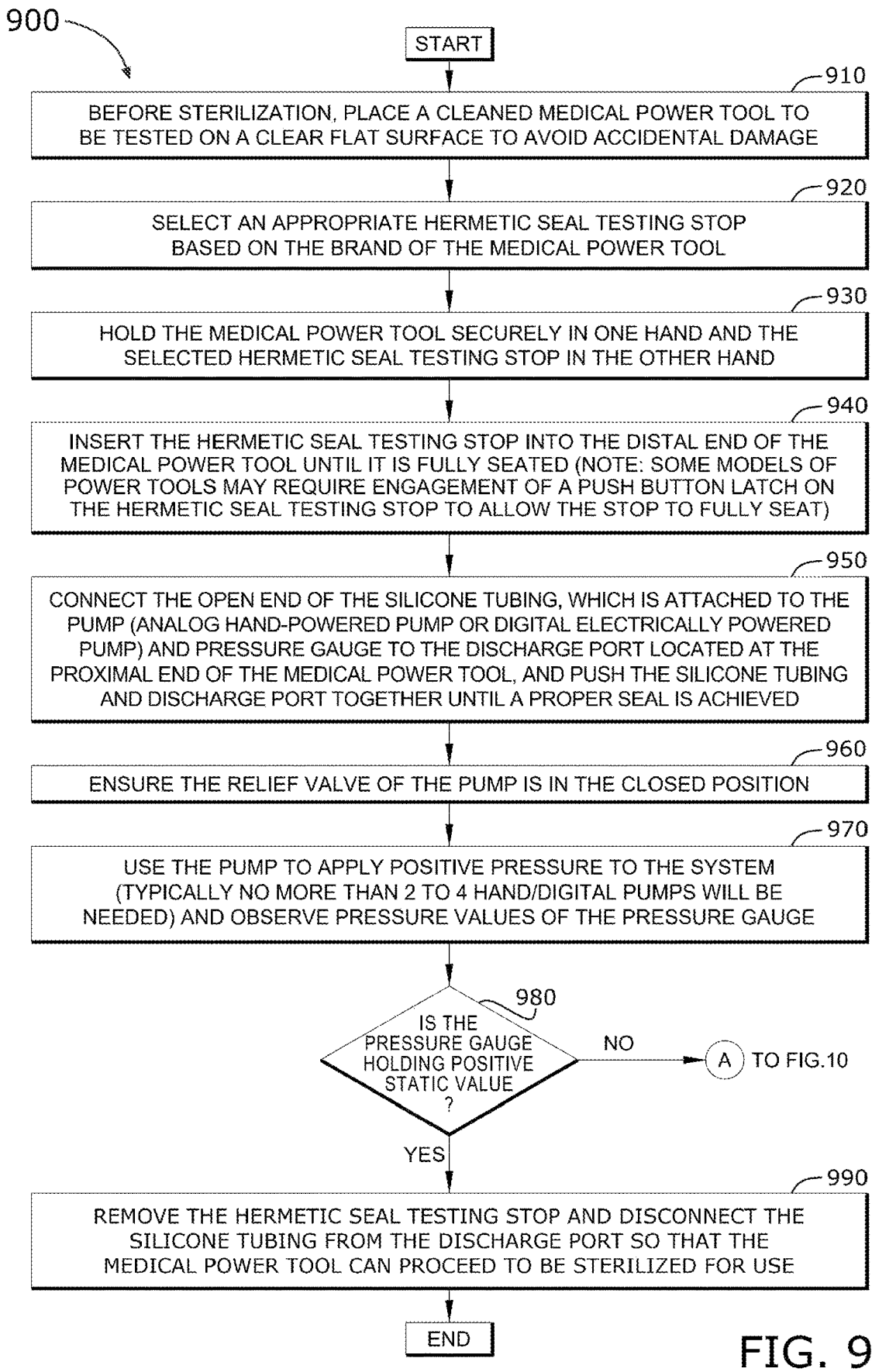
FIG. 9 conceptually illustrates a process for testing medical device integrity with a hermetic seal tester in some embodiments.
Figure 10:
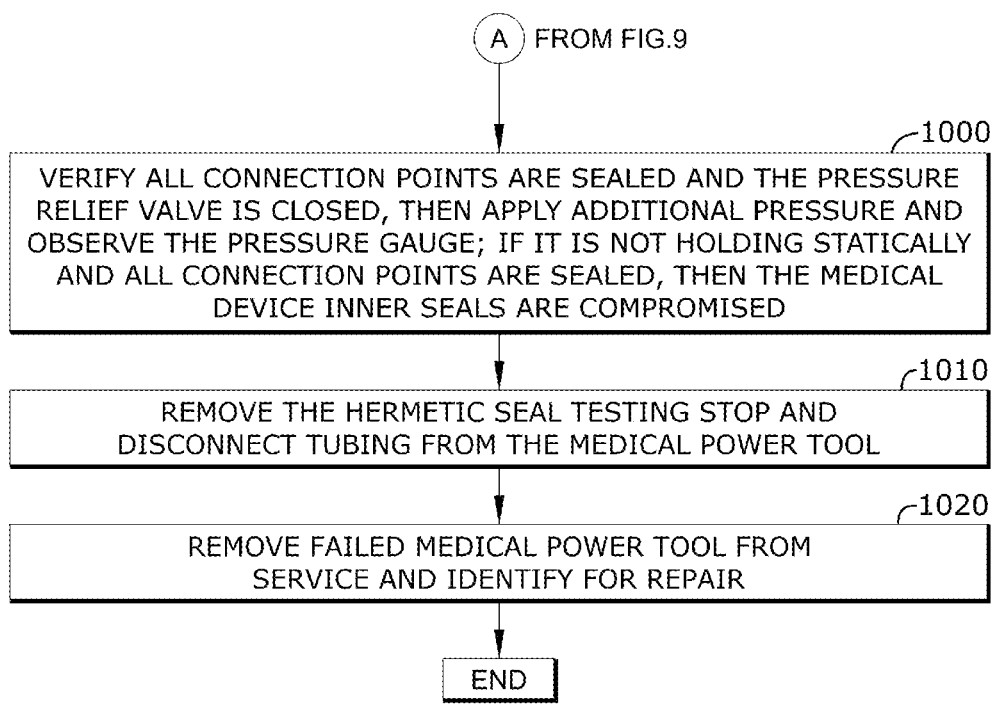
FIG. 10 conceptually illustrates a continuation of the process for testing medical device integrity with a hermetic seal tester shown in FIG. 9.

By way of example, FIGS. 9 and 10 conceptually illustrate a process for testing medical device integrity with a hermetic seal tester 900 in some embodiments. Starting with FIG. 9, as shown in this figure, the process for testing medical device integrity with a hermetic seal tester 900 begins before sterilization of a medical device or medical power tool. In this example, "medical device" and "medical power tool" are referred to collectively and/or individually as simply the "medical power tool", which is not intended to suggest that the process for testing medical device integrity with a hermetic seal tester 900 only works for medical power tools.

Figure 11:
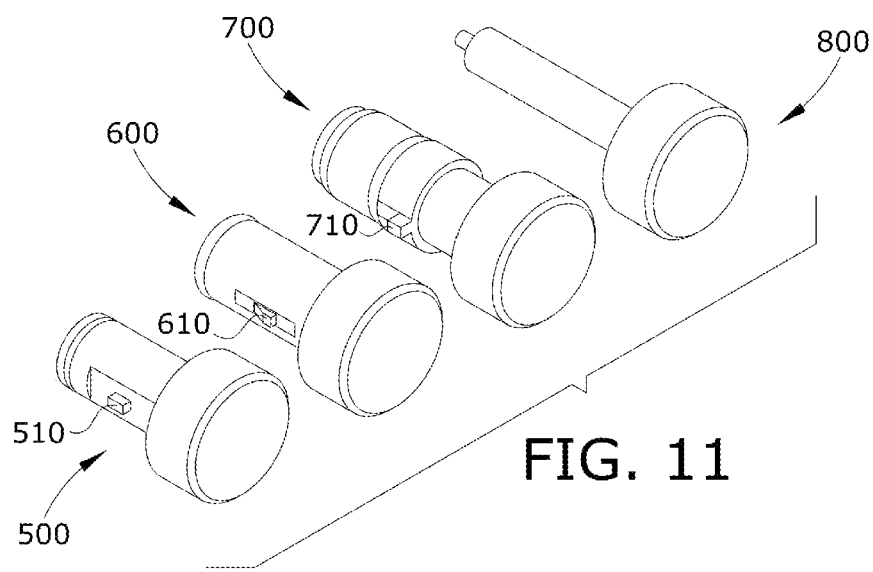
FIG. 11 conceptually illustrates a view of multiple plugs from which a selection is made according to a particular medical device to be tested by the hermetic seal tester in some embodiments.

Specifically, the process for testing medical device integrity with a hermetic seal tester 900 starts with a first step of placing a cleaned medical power tool to be tested for leaks on a clear flat surface (at 910) to avoid accidental damage while testing for leaks with the hermetic seal tester. The process for testing medical device integrity with a hermetic seal tester 900 of some embodiments then proceeds to the next step of selecting (at 920) an appropriate hermetic seal testing stop (or rather, appropriate type of nylon plug) based on the brand or type of medical power tool being tested for leaks. An example of selecting a nylon plug from a variety of different hermetic seal testing stops is described below, by reference to FIG. 11.

After the appropriate nylon plug is selected, the process for testing medical device integrity with a hermetic seal tester 900 continues on to the next step of holding the medical power tool securely in one hand (by a user) and holding the selected hermetic seal testing stop (nylon plug) in the other hand (at 930). At the next step of the process for testing medical device integrity with a hermetic seal tester 900, the user inserts the selected hermetic seal testing stop (nylon plug) into the distal end of the medical power tool until it is fully seated (at 940). A conceptual example of this step is demonstrated and described below, by reference to FIGS. 12-13. Different medical power tools may have different requirements to attach the nylon plug. For instance, some models of medical power tools may require engagement of a push button latch on the hermetic seal testing stop (nylon plug) to allow the nylon plug to be fully seated.

After inserting the nylon plug into the distal end of the medical power tool, the process for testing medical device integrity with a hermetic seal tester 900 continues on to the next step of connecting the open end of the silicon tubing for the hermetic seal tester to the discharge port of the medical power tool (located at the proximal end of the medical power tool) and then pushing the silicone tubing and discharge port together until a proper seal is achieved (at 950). An example of attaching the tubing to the discharge port is demonstrated in and described below, by reference to FIG. 14.

Figure 15:
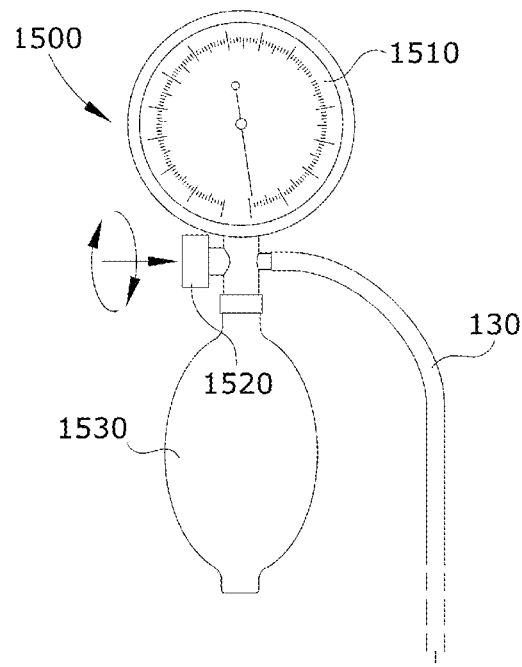
FIG. 15 conceptually illustrates a front view of the hermetic seal tester with a pressure gauge valve turning to a closed position in some embodiments.

While one end of the silicone tubing is connected to the discharge port, the other end of the silicone tubing is attached to the pump and pressure gauge of the hermetic seal tester. The pump can be an analog hand-powered pump or a digital electrically powered pump in different configurations of the hermetic seal tester. Thus, during the next step of the process for testing medical device integrity with a hermetic seal tester 900, the user would ensure that a relief valve of the pump is in the closed position (at 960). An example of closing the relief valve of the pump is described below, by reference to FIG. 15.

When the relief valve is affirmatively shut (in the closed position), then the user moves forward to the next step of the process for testing medical device integrity with a hermetic seal tester 900 which involves using the pump to apply positive pressure to the system and observing the pressure readings/values shown on the pressure gauge (at 970). Typically, the user only needs to apply two-four manual squeezes of the pump or two-four digital pressure application pumps to get the desired pressure for observation of the pressure gauge to see whether the pressure gauge is holding the positive pressure readings/values or not. An example of applying manual hand squeezes to the pump is described below, by reference to FIG. 16.

Accordingly, after applying a few positive pressure pumps into the system, the next step of the process for testing medical device integrity with a hermetic seal tester 900 involves determining (at 980) whether the pressure gauge of the hermetic seal tester is holding the positive static value/reading or not. When the pressure gauge does not hold the static pressure reading/value, the process for testing medical device integrity with a hermetic seal tester 900 proceeds to a set of steps related to verifying the presence of a leak for the medical power tool, which is described further below by reference to FIG. 10.

On the other hand, when the pressure gauge affirmatively determined (at 980) to hold/maintain the static pressure readings/values, the integrity of the medical power tool is confirmed. Once the integrity of the medical power tool is confirmed, the process for testing medical device integrity with a hermetic seal tester 900 moves to the next step of removing the hermetic seal testing stop (nylon plug) from the distal end and disconnecting the silicone tubing from the discharge port so that the medical power tool can proceed to be sterilized for use. Then the process for testing medical device integrity with a hermetic seal tester 900 ends.

Turning back to the determination (at 980), when the pressure gauge is not holding the static pressure readings/values, the process for testing medical device integrity with a hermetic seal tester 900 proceeds to the set of steps related to verifying the presence of a leak for the medical power tool, which are demonstrated in FIG. 10. Specifically, the process for testing medical device integrity with a hermetic seal tester 900 verifies the presence of a compromised seal for the medical power tool by the user verifying that all connection points between the silicone tubing and discharge port and the nylon plug and the distal tip of the channel port are sealed and that the pressure relief valve is closed, and then applying additional pressure to the pump and observing the pressure gauge readings again (at 1000). When the pressure gauge is observed to hold the static pressure readings/values, then it is likely that a connection point was compromised during the prior round. In that case, it is possible (but not required) that the user would want to replace the silicone tubing or nylon plug with newer replacements for future leak testing. On the other hand, when the pressure readings/values are not held statically, and all of the connection points have been confirmed to be sealed and the pressure relief valve is closed, then the inner seals of the medical power tool are determined (at 1000) to be compromised.

When the inner seals of the medical power tool are compromised, the process for testing medical device integrity with a hermetic seal tester 900 proceeds to the next step at which the user removes the hermetic seal testing stop (nylon plug) from the distal end and disconnects the silicone tubing from the discharge port of the medical power tool (at 1010), followed by a step at which the user removes the failed medical power tool from service and identifies the medical power tool for repair (at 1020). Then the process for testing medical device integrity with a hermetic seal tester 900 ends.

As noted above, the process for testing medical device integrity with a hermetic seal tester 900 includes a step for selecting (at 920) an appropriate hermetic seal testing stop (nylon plug) based on the brand or type of medical power tool being tested for leaks. By way of example, FIG. 11 conceptually illustrates a view of multiple plugs from which a selection is made according to a particular medical device to be tested by the hermetic seal tester in some embodiments. Specifically, the multiple plugs include the second type of nylon plug 500 with its guide tab 510, the third type of nylon plug 600 with its guide tab 610, the fourth type of nylon plug 700 with its guide tab 710, and the fifth type of nylon plug 800 which does not have a guide tab. In addition to these types of nylon plugs, the first type of nylon plug 400 or another other type of nylon plug (e.g., nylon plug 120 described above by reference to FIGS. 1-3) could be included among the multiple plugs from which the user selects one for use. The key in selecting the right nylon plug is ensuring that the selected nylon plug fits the distal end of the medical device being tested for leaks, or more specifically, fits the distal end of the medical device in a way that forms an air-tight seal.

Figure 12:
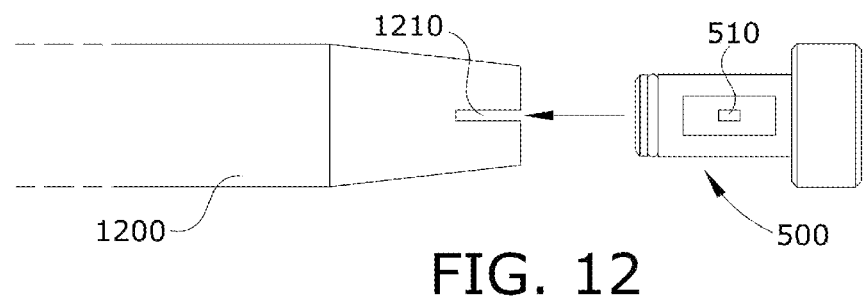
FIG. 12 conceptually illustrates a front view of placement of the selected plug in the particular medical device to be tested by the hermetic seal tester in some embodiments.
Figure 13:
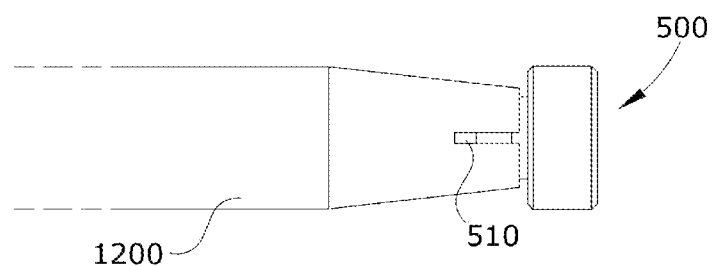
FIG. 13 conceptually illustrates a front view of the selected plug seated in the particular medical device to be tested by the hermetic seal tester in some embodiments.

Now turning to another example, FIG. 12 conceptually illustrates a front view of placement of the selected plug in the particular medical device to be tested by the hermetic seal tester in some embodiments. While the selected plug in this example is the second type of nylon plug 500, it is understood that any of the other types of nylon plugs could be selected for use with other medical devices, so long as the selected type of nylon plug fits the distal end of the medical device and forms an air tight seal. Now, as shown in this figure, the second type of nylon plug 500 is selected to fit into a particular medical device, which in this case is an arthroscopic shaver 1200 (or "bone shaver 1200"). The arthroscopic shaver 1200 has a shaver slot 1210 at the distal end of the device into which the guide tab 510 of the selected nylon plug 500 fits to connect the selected nylon plug 500 to the distal end of the bone shaver 1200. A sealed, air tight connection is made when the selected nylon plug 500 is pushed into the channel opening of the bone shaver 1200 with the guide tab 510 sliding into the shaver slot 1210. This is shown by the example in FIG. 13, which conceptually illustrates a front view of the selected plug 500 seated in the particular medical device 1200 to be tested by the hermetic seal tester in some embodiments.

Figure 14:
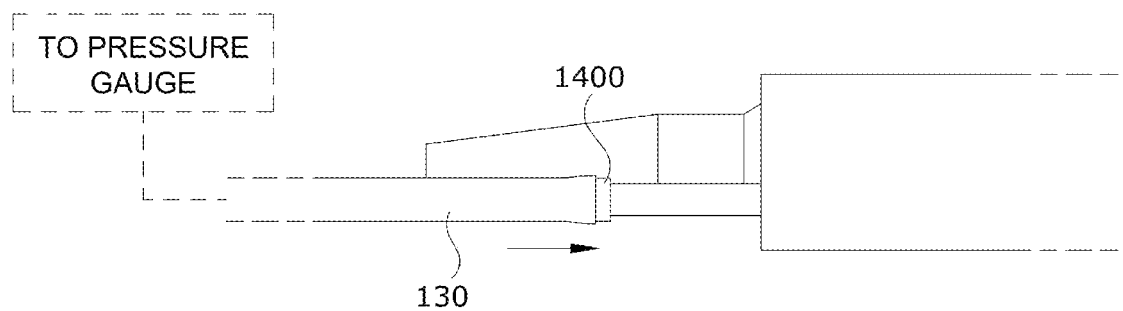
FIG. 14 conceptually illustrates a front view of a connection of the tubing of the hermetic seal tester to a discharge port of the medical device to be tested in some embodiments.

Turning to another example, FIG. 14 conceptually illustrates a front view of a connection of the tubing 130 of the hermetic seal tester to a discharge port 1400 of the medical device to be tested in some embodiments. After the hermetic seal testing stop (nylon plug) is connected to the distal end of the medical device and is sealed air tight, and after the tubing 130 is connected to the discharge port 1400, the user would close the relief valve (otherwise referred to as a "pressure gauge valve") or ensure that the relief value is in the closed position. This is demonstrated in FIG. 15, which conceptually illustrates a front view of a pressure gauge 1500 and gauge dial 1510 of the hermetic seal tester with a pressure gauge valve 1520 turned to a closed position (shown by circular arrows in this figure). Once in the pressure gauge valve 1520 is in the closed position, activation of the pump 1530 will pressurize the system through the tubing 130 and into the discharge port 1400 of the medical device being tested for leaks. On the other hand, when the pressure gauge valve 1520 is not closed, pressure will not build by activating the pump 1530, or when the pressure gauge valve 1520 is opened, pressure will be release from the system. Thus, before the hermetic seal tester can be used to test the integrity of a medical device, the pressure gauge valve 1520 needs to be set to the closed position.

Figure 16:
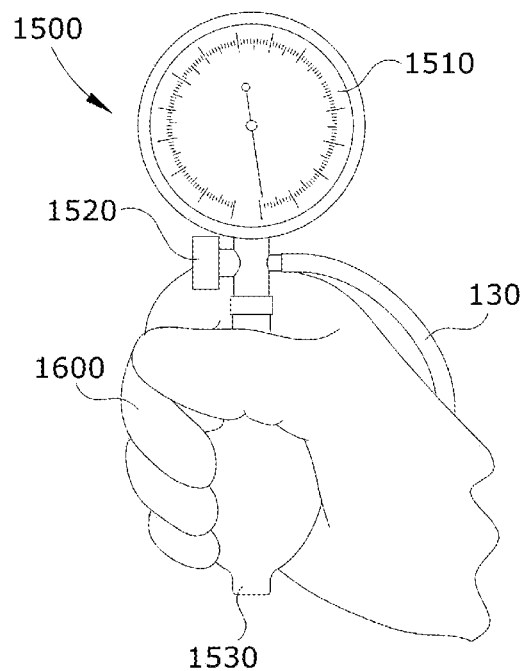
FIG. 16 conceptually illustrates a front view of the hermetic seal tester in use with a user squeezing a bulb of the hermetic seal tester in some embodiments.

Finally, FIG. 16 conceptually illustrates a front view of the hermetic seal tester in use with a user 1600 squeezing a pump 1530 of the hermetic seal tester. If the pressure gauge valve 1520 is in the closed position, the positive pressure by the user 1600 squeezing the pump 1530 will pressurize the system through tubing 130, and the pressure gauge 1500 will reflect the positive pressure on the gauge dial 1510. Specifically, the pressure in the interior channel of the medical device will increase for each pressurized pump applied by the pump (whether manual pumping by the user 1600 or electrically driven pump pressurization). If the interior channel of the medical device has any defective seals or leaks, then the gauge dial 1510 needle will show decreased pressure. Accordingly, when the positive pressure reading/value shown on the gauge dial 1510 holds the reading/value after some time, then the medical device is confirmed as having full integrity for usage during operations or other medical procedures. On the other hand, when the gauge dial 1510 shows an initial pressured reading/value that diminishes shortly after the user 1600 applies the positive pressure to the pump 1530, then channel seals have been compromised for the medical device, which would then be removed from active use and sent for repair.

The above-described embodiments of the invention are presented for purposes of illustration and not of limitation. While these embodiments of the invention have been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claims.

We claim:

1. A hermetic seal tester for medical devices comprising:
a manual hand pressure pump configured to build pressure by outward air flow when force is applied to the pump;
a pressure gauge comprising a gauge dial, a needle within the gauge dial, and an air flow channel that is operably connected to the manual hand pressure pump, wherein the air flow channel comprises an air flow tube connection port and a manual relief valve configured for manual opening and closing, wherein the manual relief valve is configured to release air flow from the manual hand pressure pump when in an open position, wherein the manual relief valve is configured to channel air flow from the manual hand pressure pump into the air flow tube connection port when in a closed position;
a hermetic seal testing stop comprising a guide tab, wherein the hermetic seal testing stop is coupled to a distal end of a fluid channel of a particular medical device being tested for leaks by sliding the guide tab into a slot along the distal end of the fluid channel of the particular medical device, wherein the hermetic seal testing stop creates an air tight seal when the guide tab is fully slid into the slot and snapped into place; and
flexible tubing comprising a connection end and an open end, wherein connection end is connected to the hand pressure pump and pressure gauge at the air flow tube connection port, wherein the open end of the flexible tubing attaches to a discharge port of the particular medical device at a proximal end of the particular medical device, wherein outward air flow from the manual hand pressure pump is channeled into the flexible tubing through the air flow tube connection port when the manual relief valve is in the closed position, wherein the air flow channeled into the flexible tubing enters the fluid channel of the particular medical device being tested for leaks through the discharge port and builds pressure when the hermetic seal testing stop is coupled to the distal end of the fluid channel of the particular medical device, wherein the needle moves within the gauge dial to show an amount of pressure building up by squeezing the manual hand pressure pump, wherein the pressure gauge is configured to monitor pressure within the particular medical device as displayed on the pressure gauge.

2. The hermetic seal tester for medical devices of claim 1, wherein the hermetic seal testing stop comprises a nylon plug.

3. The hermetic seal tester for medical devices of claim 2, wherein the nylon plug is a particular nylon plug in a plurality of nylon plugs that are used by the hermetic seal tester to test a plurality of different medical devices for leaks, wherein the particular nylon plug is configured to form the air tight seal when coupled to the distal end of the particular medical device being tested for leaks.

4. The hermetic seal tester for medical devices of claim 3, wherein the particular medical device being tested for leaks comprises a medical power tool.

5. The hermetic seal tester for medical devices of claim 4, wherein the medical power tool comprises an arthroscopic shaver.

6. A process for testing medical device integrity with a hermetic seal tester comprising:
    inserting a hermetic seal testing stop nylon plug ("nylon plug") into a distal end of a medical device being tested for leaks by a user with a hermetic seal tester, wherein the nylon plug comprises a guide tab;
    ensuring that the nylon plug forms an air-tight seal that prevent air flow out of the distal end of the medical device by sliding the guide tab into a slot along the distal end of the medical device until the nylon plug snaps into place;
    connecting an open end of tubing of the hermetic seal tester to a discharge port at a proximal end of the medical device;
    ensuring that a manually operable relief valve of a manual hand pressure pump of the hermetic seal tester is in a closed position;
    applying manual hand-powered force, by the user, to squeeze the manual hand pressure pump to increase pressure within an interior channel of the medical device;
    observing a pressure reading of a pressure gauge of the hermetic seal tester;
    determining whether the pressure gauge statically holds the pressure reading for an amount of time; and
    confirming one of (i) affirmative integrity of the medical device when the pressure gauge statically holds the pressure reading for the amount of time and (ii) no integrity of the medical device when the pressure gauge does not statically hold the pressure reading for the amount of time.

7. The process for testing medical device integrity with a hermetic seal tester of claim 6, wherein the tubing comprises flexible silicon tubing, wherein the flexible silicon tubing comprises a connected end that is connected to the manual hand pressure pump and the pressure gauge of the hermetic seal tester.

8. The process for testing medical device integrity with a hermetic seal tester of claim 6 further comprising sterilizing the medical device in preparation for use during a medical procedure when affirmative integrity of the medical device is confirmed.

9. The process for testing medical device integrity with a hermetic seal tester of claim 6, wherein the nylon plug is a first nylon plug, further comprising:
    checking integrity of the air-tight seal between the first nylon plug and the medical device and inserting a second nylon plug to snap into place at the distal end of the medical device when the integrity of the air-tight seal is not ensured by the first nylon plug; and
    removing the medical device from service when no integrity of the medical device is confirmed and the air-tight seal is not ensured by inserting both the first nylon plug and the second nylon plug.

10. The process for testing medical device integrity with a hermetic seal tester of claim 6, wherein the nylon plug comprises a particular type of nylon plug from a plurality of types of nylon plugs suitable for use with a plurality of different brands and types of medical devices.

11. The hermetic seal tester for medical devices of claim 1, wherein the pressure gauge displays the pressure within the particular medical device by moving the needle along the gauge dial as pressure builds up and by releasing the needle to a start gauge dial position when the relief valve is opened to an open position.

12. The hermetic seal tester for medical devices of claim 1, wherein the flexible tubing comprises flexible silicon tubing.

13. The hermetic seal tester for medical devices of claim 12 further comprising an O-ring to ensure the air tight seal between the hermetic seal testing stop and a channel port at the distal end of the fluid channel of the particular medical device.

14. The hermetic seal tester for medical devices of claim 1, wherein the guide tab comprises a push button latch.

* * * * *